United States Patent [19]

Murai et al.

[11] 4,162,331
[45] Jul. 24, 1979

[54] SUBSTITUTED N-(CARBOXYMETHYL)-3-AMINOPROPAN-2-OL DERIVATIVES

[75] Inventors: Hiromu Murai; Katsuya Ohata; Hiroshi Enomoto; Shoichi Chokai; Mitsuhiro Machara; Katsuhide Saito; Takayuki Ozaki, all of Kyoto, Japan

[73] Assignee: Nippon Shinyaku Co., Ltd., Japan

[21] Appl. No.: 762,021

[22] Filed: Jan. 24, 1977

Related U.S. Application Data

[62] Division of Ser. No. 692,878, Jun. 4, 1976, Pat. No. 4,064,252.

[30] Foreign Application Priority Data

Jun. 17, 1975 [JP] Japan .................................. 50-74014
Jun. 17, 1975 [JP] Japan .................................. 50-74015

[51] Int. Cl.$^2$ ............................................. C07C 103/76

[52] U.S. Cl. .................................. 424/324; 260/559 D; 260/559 A; 260/559 B; 260/559 T; 260/399; 260/404.5; 424/309; 424/311; 424/312; 424/317; 424/319; 560/16; 560/17; 560/18; 560/37; 560/41; 560/43; 560/44; 560/45; 560/251; 562/432; 562/433; 562/442; 562/455

[58] Field of Search .......... 260/559 D, 559 A, 559 B, 260/559 T, 399, 404.5; 424/324, 309, 311, 312, 317, 319; 560/41, 43, 44, 18, 37, 45, 17, 16, 251; 562/432, 433, 442, 455

[56] References Cited

U.S. PATENT DOCUMENTS

| 3,928,412 | 12/1975 | Smith | 260/559 A |
| 3,949,088 | 4/1976 | Samualson | 260/559 A |
| 3,959,369 | 5/1976 | Smith | 260/559 A |
| 4,034,106 | 7/1977 | Smith | 260/559 A |

Primary Examiner—Arthur P. Demers
Attorney, Agent, or Firm—Jacobs & Jacobs

[57] ABSTRACT

New carboxylic acid derivatives are proposed for use as agents in the treatment or prevention of arteriosclerosis. 1-(p-chlorophenoxy)-3-(N-phenyl-N-carbomethoxymethylamino)-2-propanol is a typical compound.

15 Claims, No Drawings

SUBSTITUTED N-(CARBOXYMETHYL)-3-AMINOPROPAN-2-OL DERIVATIVES

CROSS-REFERENCE

This is a division of Ser. No. 692,878 filed June 4, 1976, now U.S. Pat. No. 4,064,252.

This invention relates to new carboxylic acid derivatives having the general formula:

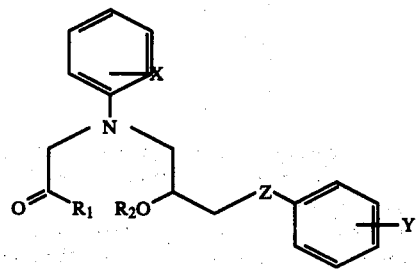

where
- Z is oxygen or sulfur,
- X is hydrogen, halogen, lower alkyl, lower alkoxy, carboxyl, lower alkoxycarbonyl or carbamoyl;
- Y is hydrogen, halogen or lower alkyl when Z is sulfur;
- Y is hydrogen, halogen, lower alkyl, lower alkoxy, aralkoxy, hydroxyl, carboxyl, lower alkoxycarbonyl or cyano when Z is oxygen; and
- $R_1$ is OR' or NR"R"', where R' is hydrogen or lower alkyl unsubstituted or substituted by at least one hydroxy or lower alkoxy and R" and R"' are independently hydrogen, lower alkyl unsubstituted or substituted by at least one hydroxy or lower alkoxy, aryl or aralkyl, or R" and R"' represent the atoms necessary to form with the nitrogen atom to which they are attached, a 5- to 7-membered saturated or unsaturated heterocyclic ring containing said nitrogen atom as the sole heteroatom or containing a second heteroatom selected from the group consisting of oxygen, nitrogen and sulfur; and
- $R_2$ is hydrogen, acyl or lower alkyl;

and pharmaceutically acceptable salts thereof.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec. butyl, tert. butyl, pentyl, isopentyl, neopentyl, tert. pentyl, hexyl, and the like. It is preferred that the lower alkyl contains from 1 to 4, most preferably 1 or 2, carbon atoms.

The term lower alkoxy denotes a univalent saturated branched or straight hydrocarbon chain containing from 1 to 6 carbon atoms joined to the rest of the molecule through an ether oxygen atom. Representative of such lower alkoxy groups are thus methoxy, ethoxy, propoxy, isopropoxy, butoxy, pentoxy, hexoxy, and the like. It is preferred that the lower alkoxy contains from 1 to 4, most preferably 1 or 2, carbon atoms.

The term lower alkoxycarbonyl denotes a univalent radical containing a lower alkoxy group joined to the rest of the molecule through a carbonyl group. It is preferred that the lower alkoxy moiety of the lower alkoxycarbonyl contains from 1 to 4, most preferably 1 or 2, carbon atoms.

The term aryl denotes an aromatic compound of 6 to 12 carbon atoms containing one or two aromatic rings composed of carbon and hydrogen atoms. Representative of such aryl groups are thus phenyl, biphenyl, naphthyl, tolyl, dimethylphenyl, trimethylphenyl, and the like. Preferably, the term aryl denotes phenyl or phenyl substituted by 1 or 2 lower alkyl.

The term aralkyl denotes a lower alkyl group substituted by aryl of 6 to 12 carbon atoms. Representative of such aralkyl groups are thus benzyl, xylyl, phenethyl, phenylbutyl, naphthylmethyl, and the like. Preferably, the aralkyl has 1 to 4, most preferably 1 or 2, carbon atoms in the alkyl moiety and the aryl moiety is phenyl.

The term acyl denotes a radical derived from an organic carboxylic acid by the removal of a hydroxy group. The organic carboxylic acid may be aliphatic, aromatic or heterocyclic. Representative acyl groups are loweralkanoyl having from 1 to 7 carbon atoms, e.g. formyl, acetyl, propanoyl, heptanoyl, and the like, said lower alkanoyl being unsubstituted or substituted by carboxy, aryloyl of 7 to 13 carbon atoms, e.g. benzoyl, naphthoyl, methylbenzoyl, and the like, or $R_4CO$— where $R_4$ is a saturated or unsaturated heterocyclic ring containing from 5 to 7 ring members and 1 or 2 hetero atoms selected from the group consisting of nitrogen, oxygen or sulfur, e.g. pyridinoyl, morpholinoyl, piperidinoyl, piperazinoyl, pyrrolidinoyl, and the like. Preferably, the term acyl denotes lower alkanoyl of 1 to 7 carbon atoms, most preferably 1 to 5 carbon atoms, unsubstituted or substituted by one carboxy, benzoyl, or $R_4CO$— where $R_4$ is a saturated or unsaturated heterocyclic ring of 5 to 7, most preferably 7, carbon atoms containing a nitrogen atom as the sole hetero atom, such as pyridinoyl.

The term aralkoxy denotes a lower alkoxy group substituted by aryl of 6 to 12 carbon atoms. Representative of such aralkoxy groups are thus phenylmethoxy, phenylethoxy, phenylpropoxy, phenylbutoxy, phenylhexoxy, tolylmethoxy, tolylbutoxy, dimethylphenylmethoxy, trimethylphenylmethoxy, naphthylmethoxy, naphthylethoxy, naphthylhexoxy, and the like. It is preferred that the alkoxy moiety of the aralkoxy contains from 1 to 4, most preferably 1 or 2, carbon atoms and that the aryl moiety is phenyl.

When X and/or Y is halogen, the halogen may be chloro, bromo, fluoro or iodo, more preferably chloro, bromo or fluoro, and most preferably, chloro or bromo.

When R" and R"' form said heterocyclic ring, the ring preferably contains 6 carbon atoms and nitrogen as the sole heteroatom or contains an oxygen atom as a second heteroatom, e.g. morpholine, piperidine, pyridine, and the like.

A sub-group of the compounds of Formula I are those in which $R_2$ is hydrogen and salts thereof. These compounds are illustrated by Formulas (II) and (II'):

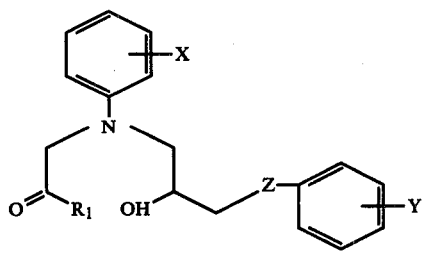
[II]

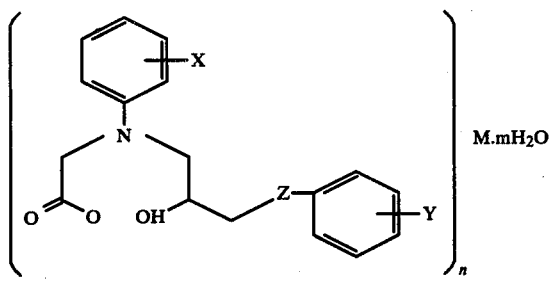
[II]' where X, Y, Z and $R_1$ are as defined above, m and n are integers of from 1 to 3 and M is alkali metal, alkaline earth metal, ammonium or substituted ammonium cation.

Compounds II and II', where $R_1$ is —OR' and R' is hydrogen may be obtained by hydrolyzing the compounds of the Formula [I]' with an alkali metal hydroxide such as sodium hydroxide and potassium hydroxide.

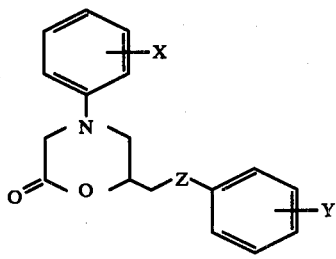
[I]'

(where X, Y and Z are as described above)

The compounds [II], where $R_1$ is —OR' and R' is lower alkyl or lower alkyl substituted by hydroxyl or lower alkoxy are obtained by treating the morpholinone derivatives having the general Formula [I]' with the corresponding alcohols (R'OH). In this case, it is effective to use either acid catalysts, such as hydrogen chloride, sulfuric, acetic acid and p-toluenesulfonic acid or basic catalysts, such as sodium metal and potassium metal to accelerate the reaction. The derivatives expressed by the general Formula [II], where $R_1$ is

and R" and R'" are as described above, are obtained by treating the morpholinone derivatives of the Formula [I]' with the corresponding amines

The reaction is carried out in the absence or presence of a polar solvent such as N,N-dimethylformamide or a hydrocarbonic solvent.

The compounds prepared in this manner have a free hydroxyl group or in the case when an alkali metal hydroxide is used for the hydrolysis, they exist as the corresponding alkali metal salts. If necessary, this alkali metal salt can be converted into the corresponding alkaline earth metal salt or aluminum salt by treatment with an alkali earth metal salt or aluminum compound (for example calcium chloride, aluminum chloride). Ammonium or organic amine salts can also be formed. New carboxylic acid derivatives thus obtained possess excellent serum lipid lowering activities.

Compounds I' are new compounds disclosed and claimed in our copending application U.S. Ser. No. 692,879, filed June 1, 1976, which is hereby incorporated herein by reference thereto. The details are reported below.

1. Blood lipid lowering activities in 8 week-old male rats having normal serum lipid content.

The values shown in Table 1 indicate the concentration changes of serum cholesterol and serum triglycride after the treatment with the shown various doses/day for 3.5 days. The mentioned compounds were orally administered to rat's groups consisting of 10 animals through a stomach tube twice a day. Blood was usually withdrawn 4 hours after the last administration. Serum cholesterol concentration was determined by the method of Levine and Zak, and triglyceride by the method of Kassler and Laderer by means of autoanalyzer. In all examples shown in Table 1, % decrease of treated groups are then to the non-treated reference group (control group), where the value of control group is represented as 100%. These compounds possess more potent serum lipid lowering activities than clofibrate at the dose of 20 mg/kg/day and 10 mg/kg/day.

Table 1

| | % decrease of serum lipid contents after the oral administration to 8 week-old male rats having the normal blood lipid content for 3.5 days. | | | | | |
|---|---|---|---|---|---|---|
| | 100 mg/kg/day | | 20 mg/kg/day | | 10 mg/kg/day | |
| compound | serum cholesterol | serum triglyceride | serum cholesterol | serum triglyceride | serum cholesterol | serum triglyceride |
| 2 | 33.5 | 72.0 | 28.8 | 73.2 | 15.5 | 53.6 |
| 4 | 39.1 | 59.0 | 23.4 | 54.4 | 22.9 | 36.5 |
| 60 | 28.8 | 51.3 | 27.5 | 47.2 | 20.9 | 39.4 |
| 6 | 41.2 | 72.4 | 34.7 | 49.6 | | |
| 11 | 30.3 | 66.0 | 21.5 | 65.4 | | |
| 18 | 14.9 | 59.3 | 12.4 | 54.5 | | |

Table 1-continued

% decrease of serum lipid contents after the oral administration to 8 week-old male rats having the normal blood lipid content for 3.5 days.

| compound | 100 mg/kg/day | | 20 mg/kg/day | | 10 mg/kg/day | |
|---|---|---|---|---|---|---|
| | serum cholesterol | serum triglyceride | serum cholesterol | serum triglyceride | serum cholesterol | serum triglyceride |
| 32 | 29.6 | 56.6 | | | | |
| 35 | 19.8 | 52.7 | | | | |
| 41 | 12.3 | 53.2 | | | | |
| clofibrate | 37.0 | 51.7 | 12.6 | 36.3 | 5.8 | 6.2 |

Note: Compound's numbers correspond to those illustrated in Table 4.

2. Blood triglyceride lowering activities in the carbohydrate induced hypertriglyceridemia of fructose loaded 9 week-old male rats.

Compounds shown in Table 2 were orally administered to the rat groups consisting of 10 animals for 3 days. Drinking of 10% fructose solution continued for 48 hours prior to sacrifice.

Fasting for 18 hours after the last administration, blood was withdrawn. In all examples shown in Table 2, % inhibitions of the treated groups are to the fructose loaded control group. The changed value of triglyoride content before and after the fructose load in the control group is represented as 100%. These compounds possess more potent inhibition activities than clofibrate.

Table 2

Hypotriglyceridemic effect in the fructose induced hypertriglyoridemic male rats.

| compound | inhibition ratio (%) | | |
|---|---|---|---|
| | 100 mg/kg/day | 30 mg/kg/day | 10 mg/kg/day |
| 4 | 93.0 | 69.9 | 46.5 |
| 6 | 85.7 | 67.6 | 55.9 |
| 10 | 63.3 | 61.5 | 48.5 |
| clofibrate | 23.2 | −2.3 | −16.6 |

Note: Compound numbers correspound to those illustrated in Table 4.

3. Blood cholesterol lowering activities in the thiouracil induced hypercholesterolemia of thiouracil loaded 9 week-old male rats.

The compounds illustrated in Table 3 were orally administered for 4 days from the 4th day to rats given 0.1% thiouracil solution for 3 days as the pretreatment. Fasting for 18 hours after the last administration, blood was withdrawn. In all examples shown in Table 3, % inhibition of treated groups are to the thiouracil loaded control group, in which the changed value of cholesterol before and after the thiouracil load is represented as 100%.

Table 3

Hypocholesterolemic effects in the thiouracil induced hypercholesterolemic male rats.

| compound | inhibition ratio (%) | | | |
|---|---|---|---|---|
| | 100 mg/kg/day | 30 mg/kg/day | 10 mg/kg/day | 3 mg/kg/day |
| 4 | 85.5 | 57.9 | 51.9 | |
| 5 | 100.7 | 69.2 | 49.9 | |
| 6 | 94.9 | 70.1 | 58.4 | |
| 10 | 94.9 | 87.4 | 52.6 | |
| L-thyroxine | | | | 54.8 |

Note: Compound numbers correspond to those illustrated in Table 4.

The following examples are given to illustrate the representative embodiment of this invention, but this invention is not limited to these examples.

EXAMPLE 1

The preparative method for 1-(p-chlorophenoxy)-3-(N-phenyl-N-carbomethoxymethylamino)-2-propanol (compound 4 of Table 4)

Thirty grams (0.095 moles) of 6-(p-chlorophenoxymethyl)-4-phenyl-2-morpholinone was added to 1.5 l methanol, the mixture was refluxed for 20 hr, a small amount of active carbon was added to the reaction mixture and filtered off. The filtrate was concentrated and the resulting residue was solidified with ether. 29.2 g of the products were obtained by filtration and dryness. Recrystallization from benzene and n-hexane gave 22.4 g of the crystals (67.5%) with a melting point of 79° to 80.5°.

elemental analysis: $C_{18}H_{20}ClNO_4$

| | C | H | N | Cl |
|---|---|---|---|---|
| calcd | 61.80 | 5.76 | 4.00 | 10.13 |
| found | 62.00 | 6.09 | 3.98 | 10.26 |

EXAMPLE 2

The preparative method for 1-(p-chlorophenoxy)-3-(N-isopropylamino carbonylmethyl-N-phenylamino)-2-propanol (compound 36 of Table 4)

After 7.0 g (0.22 moles) of 6-(p-chlorophenoxymethyl)-4-phenyl-2-morpholinone and 20 g of isopropylamine were dissolved in 50 ml of dioxane and the resulting Solution was left to stand overnight at room temperature, the reaction mixture was concentrated in vacuo. The residue was solidified by addition of a small amount of ether. The solid was filtered, washed with ether and dried to give 8.7 g of the product. Recrystallization from ethanol afforded 5.5 g (66.3%) of crystals, with a melting point of 140.5° to 142.5°.

| | C | H | N | Cl |
|---|---|---|---|---|
| calcd | 63.73 | 6.68 | 7.43 | 9.40 |
| found | 63.48 | 6.78 | 7.43 | 9.42 |

EXAMPLE 3

The preparative method for calcium [N-(3-p-chlorophenoxy-2-hydroxypropyl)-N-phenylamino] acetate monohydrate (compound 45 of Table 4)

Twenty grams (0.063 moles) of 6-(p-chlorophenoxymethyl)-4-phenyl-2-morpholinone and 2.52 g (0.063 moles) of sodium hydroxide were suspended in 200 ml of water and heated at 90° to 100° for 1 hr. The reaction mixture was hydrolyzed and dissolved. A small amount of insoluble materials was filtered off. Separately, 3.50 g (0.0315 moles) of calcium chloride was dissolved in 50 ml of water. Rapid addition of this solution to the above filtrate afforded precipitates. After stirring for 1 hr, the precipitates were collected by filtration and washed with water and dried (23.2 g). Recrystallization from acetone gave 16.9 g of crystals with a melting point of 182° to 184°.

elemental analysis: $C_{34}H_{36}Cl_2N_2O_9Ca$

|  | C | H | N | Cl |
|---|---|---|---|---|
| calcd | 56.12 | 4.98 | 3.85 | 9.74 |
| found | 56.21 | 4.92 | 3.62 | 9.78 |

A series of the compounds [II] were prepared with the same procedure. They are described in Table 4. Compounds 45 and 46 in the table are embodiments of the compounds [II]′, namely the salts of [II].

Table 4

(1) Z = O

| Compound number | X | Y | R₁ | Formula | M.W. | MP. (°C.) |
|---|---|---|---|---|---|---|
| 1 | H | H | —ONa | $C_{17}H_{18}NO_4Na$ | 323.33 | 90–93 |
| 2 | H | p-Cl | —OH | $C_{17}H_{18}ClNO_4$ | 335.79 | 114–115 |
| 3 | H | p-Cl | —ONa | $C_{17}H_{17}ClNO_4Na$ | 357.79 | 45–47 |
| 4 | H | p-Cl | —OCH₃ | $C_{18}H_{20}ClNO_4$ | 349.82 | 79–80 |
| 5 | H | p-Cl | —OCH₂CH₃ | $C_{19}H_{22}ClNO_4$ | 363.85 | 54.5–56.5 |
| 6 | H | p-Cl | —OCH₂CH₂CH₃ | $C_{20}H_{24}ClNO_4$ | 377.85 | 63.5–64.5 |
| 7 | H | p-Cl | —OCH(CH₃)₂ | $C_{20}H_{24}ClNO_4$ | 377.85 | 82.5–83 |
| 8 | H | p-Cl | —OCH₂CH₂OH | $C_{19}H_{22}ClNO_5$ | 379.85 | 88–89 |
| 9 | H | p-Cl | —OCH₂CH₂OCH₃ | $C_{20}H_{24}ClNO_5$ | 393.88 | 68–69 |
| 10 | H | p-Cl | —OCH₂CH₂CH₂CH₃ | $C_{21}H_{26}ClNO_4$ | 391.90 | 54.5–56 |
| 11 | H | o-Cl | —OCH₃ | $C_{18}H_{20}ClNO_4$ | 349.82 | 82–83 |
| 12 | H | p-CH₃ | —OCH₃ | $C_{19}H_{23}NO_4$ | 329.38 | 62–64 |
| 13 | H | p-OCH₃ | —OCH₃ | $C_{19}H_{23}NO_5$ | 345.38 | 64.5–66 |
| 14 | H | p-COOCH₃ | —OCH₃ | $C_{20}H_{23}NO_6$ | 373.37 | 107.5–108.5 |
| 15 | H | p-Br | —OCH₃ | $C_{18}H_{20}BrNO_4$ | 394.27 | 85–86 |
| 16 | H | p-F | —OCH₃ | $C_{18}H_{20}FNO_4$ | 333.37 | 63.5–65 |
| 17 | H | p-t-Bu | —ONa | $C_{21}H_{26}NO_4Na$ | 379.45 | 110–112 |
| 18 | H | p-t-Bu | —OCH₃ | $C_{22}H_{29}NO_4$ | 371.48 | (oil) |
| 19 | p-Cl | p-Cl | —ONa | $C_{17}H_{16}Cl_2NO_4Na$ | 392.22 | 56–59 |
| 20 | p-Cl | p-Cl | —OCH₃ | $C_{18}H_{19}Cl_2NO_4$ | 384.26 | 90–91 |
| 21 | p-Cl | p-t-Bu | —OCH₃ | $C_{22}H_{28}ClNO_4$ | 405.92 | (oil) |
| 22 | p-Cl | p-t-Bu | —ONa | $C_{21}H_{25}ClNO_4Na$ | 413.89 | 130–132 |
| 23 | m-Cl | p-Cl | —OCH₃ | $C_{18}H_{19}Cl_2NO_4$ | 384.26 | 90.5–91.5 |
| 24 | m-Cl | m-CH₃ | —OCH₃ | $C_{19}H_{22}ClNO_4$ | 363.83 | (oil) |
| 25 | m-Cl | p-COOCH₃ | —OCH₃ | $C_{20}H_{22}ClNO_6$ | 407.86 | 96.5–97 |
| 26 | p-CH₃ | p-Cl | —OCH₃ | $C_{19}H_{22}ClNO_4$ | 363.84 | 77–79 |
| 27 | m-OCH₃ | p-Cl | —OCH₃ | $C_{19}H_{22}ClNO_5$ | 379.85 | 75–76 |
| 28 | m-OCH₃ | p-CH₃ | —OCH₃ | $C_{20}H_{25}ClNO_5$ | 359.41 | 79–80 |
| 29 | p-COOCH₃ | H | —OCH₃ | $C_{20}H_{23}NO_6$ | 373.37 | 102–104 |
| 30 | p-COOCH₃ | p-Cl | —OCH₃ | $C_{20}H_{22}ClNO_6$ | 407.84 | 118–120 |
| 31 | p-COOC₂H₅ | o-CH₃ | —OCH₃ | $C_{21}H_{24}ClNO_6$ | 421.88 | 103–105 |
| 32 | H | p-Cl | —NH₂ | $C_{17}H_{19}ClN_2O_3$ | 334.80 | 146–147 |
| 33 | H | p-Cl | —NHCH₃ | $C_{18}H_{21}ClN_2O_3$ | 348.82 | 152–153 |
| 34 | H | p-Cl | —N(CH₃)₂ | $C_{19}H_{23}ClN_2O_3$ | 362.84 | 136.5–138 |
| 35 | H | p-Cl | —N(CH₂CH₃)₂ | $C_{21}H_{27}ClN_2O_3$ | 390.89 | 140–141.5 |
| 36 | H | p-Cl | —NHCH(CH₃)₂ | $C_{20}H_{25}ClN_2O_3$ | 376.88 | 140.5–142.5 |
| 37 | H | p-Cl | —N(morpholino) | $C_{21}H_{25}ClN_2O_3$ | 404.90 | 153.5–154.5 |
| 38 | H | p-Cl | —N(piperidino) | $C_{22}H_{27}ClN_2O_3$ | 402.92 | 107–Cl |
| 39 | H | p-Cl | —NHCH₂CH₂OH | $C_{19}H_{23}ClN_2O_4$ | 378.87 | 135–136 |
| 40 | H | p-Cl | —NHCH₂COOC₂H₅ | $C_{21}H_{25}ClN_2O_5$ | 420.89 | 98–99 |

Table 4-continued

| | | | | | | |
|---|---|---|---|---|---|---|
| 41 | H | p-Cl | —NHCH$_2$—C$_6$H$_5$ | C$_{24}$H$_{25}$ClN$_2$O$_3$ | 424.94 | (oil) |
| 42 | H | p-Cl | —Cl CH(CH$_3$)—C$_6$H$_5$ | C$_{25}$H$_{27}$ClN$_2$O$_3$ | 438.96 | (oil) |
| 43 | H | p-Cl | —NH—(2,6-(CH$_3$)$_2$C$_6$H$_3$) | C$_{25}$H$_{27}$ClN$_2$O$_3$ | 438.96 | 149.5–151 |
| 44 | H | p-t-Bu | —NH—(2,6-(CH$_3$)$_2$C$_6$H$_3$) | C$_{29}$H$_{36}$N$_2$O$_3$ | 461.61 | 119.5–121 |
| 45 | | | [Ca complex structure] Ca·H$_2$O | C$_{34}$H$_{36}$Cl$_2$N$_2$O$_9$Ca | 727.65 | 182–184 |
| 46 | | | [Al complex structure] Al·3H$_2$O | C$_{51}$H$_{53}$Cl$_3$N$_3$O$_{13}$Al | 1085.41 | no clear m.p. |

(2) Z = S

| | | | | | | |
|---|---|---|---|---|---|---|
| 47 | H | p-Cl | —OCH$_3$ | C$_{18}$H$_{20}$ClNO$_3$S | 365.88 | 76–78.5 |
| 48 | m-OCH$_3$ | p-Cl | —OCH$_3$ | C$_{19}$H$_{22}$ClNO$_4$S | 395.89 | 84.5–86 |
| 49 | p-CH$_3$ | p-CH$_3$ | —OCH$_3$ | C$_{20}$H$_{25}$NO$_3$S | 359.47 | oil |

A second sub-group of compounds (I) are those in which R$_2$ is R$_3$, namely acyl or lower alkyl. Such compounds are represented by Formula [IV] and may be:

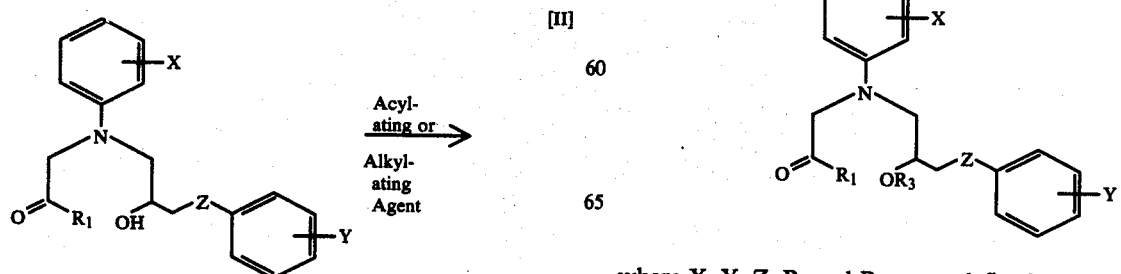

where X, Y, Z, R$_1$ and R$_3$ are as defined above.

The acylation or alkylation reaction may be carried out by the use of an acylating agent, such as acetic anhydride, succinic anhydride, benzoyl chloride and nicotinoyl chloride or an alkylating agent, such as methyl iodide.

In the case of acylation, it is preferable to use an organic base such as pyridine or triethylamine for the removal of the acid formed. In the case of alkylation, the reaction proceeds at a lower temperature of 10° in an inactive solvent such as ether and benzene.

Table 5 shows the blood lipid lowering activities in 8-week old male rats having normal serum lipid content of representative compounds IV and a prior art compound.

Table 5

| | \% decrease of serum lipid after the oral administration to the male rats having normal blood lipid content for 3.5 days. | | | |
|---|---|---|---|---|
| | 100 mg/kg/day | | 20 mg/kg/day | |
| compound | serum cholesterol | serum triglyoride | serum cholesterol | serum triglycerice |
| 50 | 30.3 | 66.0 | 21.5 | 65.4 |
| 57 | 14.9 | 59.3 | 12.4 | 54.5 |
| clofibrate | 37.0 | 51.7 | 12.6 | 36.3 |

(Compounds in Table 5 correspond to those shown in Table 6)

The values shown in Table 5 indicate the concentration changes of serum cholesterol and the triglyceride after the treatment with the shown various doses per day for 3.5 days. These compounds were orally administered to rat groups consisting of 10 animals through a stomach tube twice a day. Blood was usually withdrawn 4 hours after the last administration. Serum cholesterol concentration was determined by the method of Levine and Zak, and serum triglyceride by the method of Kessler and Lederer by means of autoanalyzer. In all examples shown in Table 1, % decrease of the treated groups are to the non-treated control group where the value of control group is represented as 100%. These compounds possess more potent serum lipid lowering activities than clofibrate at a dose of 20 mg/kg/day. The following examples are given to illustrate the representative embodiment of this invention, but this invention is not limited to these examples.

EXAMPLE 4

The preparative method for 2-acetoxy-1-(p-chlorophenoxy)-3-(N-carbomethoxymethyl-N-phenylamino) propane (compound 50 of Table 6)

After 5.5 g (0.0157 moles) of 1-(p-chlorophenoxy)-3-(N-carbomethoxymethyl-N-phenylamino)-2-propanol and 6.0 g (0.059 moles) of acetic anhydride were dissolved in 30 ml of pyridine and left to stand at the room temperature for 20 hr, the reaction mixture was concentrated. The resulting residue was poured into iced water to afford precipitates. The precipitates were collected by filtration, washed with water and dried. Recrystallization from isopropanol gave 5.1 g (83%) of the crystals, m.p. 82°–83°.

| elemental analysis: $C_{20}H_{22}ClNO_5$ | | | | |
|---|---|---|---|---|
| | C | H | N | Cl |
| calcd | 61.30 | 5.65 | 3.57 | 9.04 |
| found | 61.42 | 5.63 | 3.65 | 9.13 |

EXAMPLE 5

The preparative method for 2-acetoxy-1-(p-chlorophenylthio)-3-(N-carbomethoxymethyl-N-phenylamino) propane (compound 63 of Table 6)

After 200 mg (0.00054 moles) of 1-(p-chlorophenylthio)-3-(N-carbomethoxymethyl-N-phenylamino)-2-propanol and 1 g of acetic anhydride were dissolved in 3 ml of pyridine and left to stand at room temperature for 20 hr, the reaction mixture was poured into iced water and extracted with ether. The ether layer was washed with 10% hydrochloric acid and water and dried. Evaporation or ether under reduced pressure gave 190 mg (86.5%) of an oily substance.

| elemental analysis: $C_{20}H_{22}ClNO_4S$ | | | | | |
|---|---|---|---|---|---|
| | C | H | N | Cl | S |
| calcd | 58.88 | 5.43 | 3.43 | 8.69 | 7.86 |
| found | 58.67 | 5.54 | 3.38 | 8.75 | 7.75 |

A series of the compounds [IV] were prepared by the same procedure. They are described in Table 6. Compounds IV have excellent activity in lower mg serum lipid levels and are useful in the prevention and treatment of arteriosclerosis.

Table 6

| (1) Z = O Compounds number | X | Y | $R_1$ | $R_3$ | Formula | M.W. | MP. (°C.) |
|---|---|---|---|---|---|---|---|
| 50 | H | p-Cl | —OCH$_3$ | —COCH$_3$ | $C_{20}H_{22}ClNO_5$ | 391.86 | 82–83 |
| 51 | H | p-Cl | —OCH$_2$CH$_3$ | —COCH$_3$ | $C_{21}H_{24}ClNO_5$ | 405.88 | 89–90.5 |
| 52 | H | p-Cl | —OCH$_2$CH$_2$CH$_3$ | —COCH$_3$ | $C_{22}H_{26}ClNO_5$ | 419.91 | 69–70.5 |
| 53 | H | p-Cl | —OCH(CH$_3$)$_2$ | —COCH$_3$ | $C_{22}H_{26}ClNO_5$ | 419.91 | 69–71 |
| 54 | H | p-Cl | —OCH$_2$CH$_2$CH$_2$CH$_3$ | —COCH$_3$ | $C_{23}H_{28}ClNO_5$ | 433.93 | 81–82.5 |
| 55 | H | p-Cl | —OCH$_2$CH$_2$CH$_3$ | —COCH$_3$ | $C_{22}H_{26}ClNO_6$ | 435.90 | 57–59 |
| 56 | H | p-Cl | —OCH$_3$ | 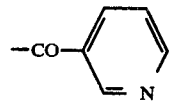 | $C_{24}H_{23}ClN_2O_5$ | 454.90 | 96–97 |

Table 6-continued

| Compound number | X | Y | R₁ | R₃ | Formula | M.W. | MP: (°C.) |
|---|---|---|---|---|---|---|---|
| 57 | H | p-Cl | —OCH₂CH₃ | —CO—(pyridyl) 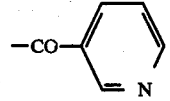 | C₂₅H₂₅ClN₂O₅ | 468.93 | 101–102 |
| 58 | H | p-Cl | —OCH₂CH₂CH₃ | —CO—(pyridyl) 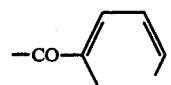 | C₂₆H₂₇ClN₂O₅ | 482.97 | 93–95 |
| 59 | H | p-Cl | —OCH(CH₃)₂ 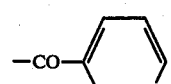 | —CO—(pyridyl) 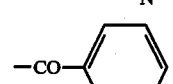 | C₂₆H₂₇ClN₂O₅ | 482.97 | 113–115.5 |
| 60 | H | p-Cl | —OCH₂CH₂CH₂CH₃ | —CO—(pyridyl) 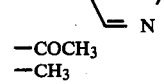 | C₂₇H₂₉ClN₂O₅ | 499.98 | 89–90 |
| 61 | H | p-t-Bu | —OCH₃ | —COCH₃ | C₂₄H₃₁NO₅ | 413.50 | 102–104.5 |
| 62 | H | p-Cl | —OH | —CH₃ | C₁₈H₂₀ClNO₄ | 349.82 | 98–99.5 |

(2) Z = S

| Compounds number | X | Y | R₁ | R₃ | Formula | M.W. | MP: (°C.) |
|---|---|---|---|---|---|---|---|
| 63 | H | p-Cl | —OCH₃ | —COCH₃ | C₂₀H₂₂ClNO₄S | 407.92 | (oil) |

The compounds (I) of the invention may be used as such or in combination with a pharmaceutically acceptable solid or liquid inert diluent or carrier in the same dosage and in the same routes of administration as conventional agents for reducing serum cholesterol and triglycerides and for prevention of arteriosclerosis in humans and other animals. The daily dosage will be determined by the physician for the particular patient, but generally a daily dosage of from about 50 mg to about 5 grams will be satisfactory, preferably about 100 mg to about 2 grams.

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

As indicated, the present invention also pertains to the physiologically acceptable salts of compounds II with alkali metals, alkaline earth metals, aluminum, ammonia and organic amines as, for example, the sodium salt, the potassium salt, the calcium salt, the aluminum salt, and the salts with amines such as ethylamine, triethylamine, ethanolamine, diethylaminoethanol, ethylenediamine, piperidine, morpholine, 2-piperidinoethanol, benzylamine, procaine, and the like.

The present invention also pertains to the physiologically acceptable non-toxic acid addition salts when X or Y is carbamoyl. Such salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

What is claimed is:

1. A compound of the formula:

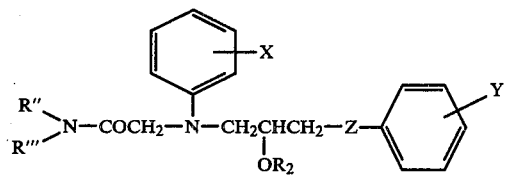

wherein

Z is oxygen or sulfur;

X is hydrogen, halogeno, lower alkyl, lower alkoxy, carboxy, carbo(lower alkoxy) or carbamoyl;

Y, when Z is sulfur, is hydrogen, halogeno or lower alkyl, or, when Z is oxygen, hydrogen, halogeno, lower alkyl, lower alkoxy, aralkoxy, hydroxy, carboxy, or carbo(lower alkoxy);

$R_2$ is hydrogen, lower alkyl or alkanoyl of 1 to 7 carbon atoms; and each of R'' and R''' taken independently is hydrogen, phenyl, unsubstituted or substituted with up to two methyl groups, or lower alkyl unsubstituted or substituted by hydroxy, lower alkoxy, carbo(lower alkoxy) or phenyl, and the pharmaceutically acceptable salts thereof.

2. A compound according to claim 1 wherein

Z is oxygen;

X is hydrogen, chloro, methyl, methoxy, carbomethoxy or carboethoxy;

Y is hydrogen, chloro, bromo, fluoro, methyl, t-butyl, methoxy or carbomethoxy; and $R_2$ is hydrogen.

3. A compound according to claim 2 wherein X is hydrogen and Y is chloro in the para-position.

4. The compound according to claim 3 wherein R'' and R''' are both hydrogen.

5. The compound according to claim 3 wherein R'' is hydrogen and R''' is methyl.

6. The compound according to claim 3 wherein R'' and R''' are both methyl.

7. The compound according to claim 3 wherein R'' and R''' are both ethyl.

8. The compound according to claim 3 wherein R'' is hydrogen and R''' is isopropyl.

9. The compound according to claim 3 wherein R'' is hydrogen and R''' is 2-hydroxyethyl.

10. The compound according to claim 3 wherein R'' is hydrogen and R''' is carbethoxymethyl.

11. The compound according to claim 3 wherein R'' is hydrogen and R''' is benzyl.

12. The compound according to claim 3 wherein R'' is hydrogen and R''' is 1-phenylethyl.

13. The compound according to claim 3 wherein R'' is hydrogen and R''' is 2,6-dimethylphenyl.

14. A pharmaceutical composition for reducing serum cholesterol and triglycerides, which comprises a serum cholesterol- and triglyceride-reducing amount of the compound of claim 1 in combination with a pharmaceutically acceptable solid or liquid inert carrier.

15. A method of reducing serum cholesterol and triglycerides, which comprises administering to an animal or human in need thereof a serum cholesterol- and triglyceride-reducing amount of the compound of claim 1.

* * * * *

UNITED STATES PATENT AND TRADEMARK OFFICE
CERTIFICATE OF CORRECTION

PATENT NO. : 4,162,331
DATED : July 24, 1979
INVENTOR(S) : Hiromu Murai et al.

It is certified that error appears in the above-identified patent and that said Letters Patent are hereby corrected as shown below:

In Column 5, the first column of Table 1 - continued and the "Note" should read as follows:

| compound |
| --- |
| 18* |
| 20* |
| 26* |
| clofibrate |

Note: * Compound's numbers correspond to those illustrated in Table 4.
\*\* Compound's numbers correspond to those illustrated in Table 6.

UNITED STATES PATENT AND TRADEMARK OFFICE
CERTIFICATE OF CORRECTION

PATENT NO. : 4,162,331
DATED : July 24, 1979
INVENTOR(S) : Hiromu Murai et al.

It is certified that error appears in the above-identified patent and that said Letters Patent are hereby corrected as shown below:

In Column 4, the first column of Table 1 should read as follows:

| compound |
|---|
| 2* |
| 4* |
| 45* |
| 6* |
| 50** |
| 57** |

Signed and Sealed this

Ninth Day of June 1981

[SEAL]

Attest:

RENE D. TEGTMEYER

Attesting Officer — Acting Commissioner of Patents and Trademarks